United States Patent [19]

Costello et al.

[11] Patent Number: 5,280,125

[45] Date of Patent: Jan. 18, 1994

[54] CHEMICAL PROCESS FOR THE PREPARATION OF 3-ALKYLATED INDOLE

[75] Inventors: Gerard F. Costello, Macclesfield, England; Stephen A. Brook, Macclesfield, England; Peter J. Harrison, Macclesfield, England

[73] Assignee: Imperial Chemical Industries PLC, London, England

[21] Appl. No.: 803,315

[22] Filed: Dec. 4, 1991

[30] Foreign Application Priority Data

Dec. 5, 1990 [GB] United Kingdom ............... 9026427

[51] Int. Cl.$^5$ ........................................ C07D 209/04
[52] U.S. Cl. ........................................... 548/491
[58] Field of Search .................................. 548/491

[56] References Cited

U.S. PATENT DOCUMENTS

| | | | |
|---|---|---|---|
| 3,732,245 | 5/1973 | Batcho et al. | 260/319.1 |
| 3,976,639 | 8/1976 | Batcho et al. | 260/240 |
| 3,979,410 | 9/1976 | Fryer et al. | 260/326 |
| 4,137,404 | 1/1979 | Batcho et al. | 542/442 |
| 4,665,087 | 5/1987 | Vlattas | 548/491 |
| 4,859,692 | 8/1989 | Bernstein et al. | 514/381 |
| 4,918,094 | 4/1990 | Bernstein et al. | 514/419 |
| 5,180,728 | 1/1993 | Kato et al. | 548/491 |

FOREIGN PATENT DOCUMENTS 0432984 6/1991 European Pat. Off. ........... 514/41.9

OTHER PUBLICATIONS

CA99:158298g The [1+4]... 1-hydroxypyrroles Foucaud et al., p. 606, (1983).
CA 107:197736b In situ... olefins, Chikashita et al., pp. 704-705, (1987).
CA113:152995t Betaines... catalysts. Goldberg et al, p. 837, (1990).
CA114:7251p Preparation... β-enamides. Cesa et al. p. 716, (1991).
CA 115:36032n Reactions... heterocycles. Clarke et al. p. 976 (1991).
Batcho, A. D.; Leimgruber, W., Indoles from 2-Methylnitrobenzenes by Condensation with Formamide Acetals Followed by Reduction: 4-Benzyloxyindole, Org. Syn. (1985), 63, 214-225.
Acheson, R. M. et al., An Imrpoved Preparation of 1-Hydroxyindole and the Synthesis of Some Related 3-Carboxylic Acids and 1-Methoxyindole—3-acetonitrile, J. Chem. Research (S) (1984), 101.
Hengarter U. et al., New Syntheses of Racemic Tryptophans, J. Org. Chem. (1979), 44, 3748-3752.
Pindur, U. et al., Synthetically Attractive Indolization Processes and Newer Methods for the Preparation of Selectively Substituted Indoles, J. Heterocycl. Chem. (1988), 25, 1-8.
Jensen, B. L. et al., Am Improved Enamine-Alkylation Procedure, Synthesis of 1-Benzyl-2-indanones and 1-Benzyl-2-tetralones, Synthesis (1977), 848-849.

Primary Examiner—Mary C. Lee
Assistant Examiner—Joseph K. McKane
Attorney, Agent, or Firm—Thomas E. Jackson

[57] ABSTRACT

A process for the preparation of a 3-alkylated indole, which comprises:
a) reacting a N-(2-nitrostyryl) enamine with an alkylating agent to afford an imine salt,
b) optionally reacting the imine salt with water to afford a (2-nitrophenyl)acetaldehyde, and
c) reacting the imine salt or the (2-nitrophenyl)acetaldehyde with a reducing agent capable of selectively reducing the nitro group, to afford the desired 3-alkylated indole.

12 Claims, No Drawings

CHEMICAL PROCESS FOR THE PREPARATION OF 3-ALKYLATED INDOLE

The present invention relates to a novel process for the preparation of certain 3-substituted indoles, and to certain intermediates which are useful in this process.

3-Substituted indoles are useful as chemical intermediates, for example in the preparation of pharmaceuticals. Examples of such pharmaceuticals include compounds disclosed in European Patent Applications publication numbers EP-A2-0199543 and EP-A2-0220066. Other pharmaceuticals include those based upon the 3-substituted indoles tryptophan, serotonin and melatonin.

It is known that indoles may be alkylated at the 3-position, for example by reaction with an alkyl halide. However, the reaction often proceeds with some difficulty, and may be accompanied by alkylation at the 1- and/or 2-position.

U.S. Pat. No. 3,976,639 discloses a process for preparing 3-unsubstituted indoles which comprises reacting a N-(2-nitrostyryl) enamine with a reducing agent capable of selectively reducing the nitro group. It is noted at column 6, lines 49 to 52 that the 3-unsubstituted indoles can be utilised as intermediates in the preparation of tryptophan and and serotonin, both of which are 3-substituted indoles.

The invention provides a process for the preparation of a 3-alkylated indole, which comprises:
a) reacting a N-(2-nitrostyryl) enamine with an alkylating agent to afford an imine salt;
b) optionally reacting the imine salt with water to afford a (2-nitrophenyl)acetaldehyde, and
c) reacting the imine salt or the (2-nitrophenyl)acetaldehyde with a reducing agent capable of selectively reducing the nitro group, to afford the desired 3-alkylated indole.

The process according to the invention has been found to afford 3-alkylated indoles in improved yield, without contamination by 1- and/or 2-alkylated indoles.

In the process, the imine salt is preferably reacted with water to afford a (2-nitrophenyl)acetaldehyde. The aldehyde is a stable intermediate, unlike the imine salt, and hence can readily be handled on a manufacturing scale.

The N-(2-nitrostyryl) enamine used in the process according to the invention is a tertiary amine having a (2-nitrostyryl) group as one of the substituents of the nitrogen atom of the tertiary amino group. Thus it is a 2-nitro-$\beta$-(disubstituted amino)styrene. The remaining two substituents of the nitrogen atom are preferably alkyl groups, for example (1—4C) alkyl groups such as methyl or ethyl, or the two ends of a 4- or 5-membered alkylene or heteroalkylene chain, thereby forming a 5- or 6-membered ring such as a pyrrolidine, piperidine or morpholine ring. Accordingly, the N-(2-nitrostyryl) enamine may be, for example, a 2-nitro-$\beta$-(di(1–4C)alkylamino)styrene such as a 2-nitro-$\beta$-(dimethylamino)styrene or a 2-nitro-$\beta$-(diethylamino)styrene, or a 2-nitro-$\beta$-(1-pyrrolidinyl)styrene, a 2-nitro-$\beta$-(1-piperidinyl)styrene or a 2-nitro-$\beta$-(4-morpholinyl)syrene.

The (2-nitrostyryl) group in the N-(2-nitrostyryl) enamine may carry one or more substituents on the benzene ring, provided that none of these interfere with any of the steps in the process according to the invention. Thus, for example, the 2-nitrostyryl group may be substituted on the benzene ring by one or more substituents selected from halogen, alkyl, alkoxy, haloalkyl, haloalkoxy, cycloalkyl, aryl, heteroaryl, aryloxy, aralkyloxy, alkoxycarbonyl, carboxy, aralkyloxycarbonyl, acyl, acyloxy, nitro, acylamino, cycloalkoxycarbonylamino, aralkylamino, cyano, alkenyl, cycloalkenyl, alkynyl and carbamoyl.

Unless otherwise stated, where reference is made in this specification to a halogen atom, as such or in a group such as a haloalkyl or haloalkoxy group, this may be, for example, a fluorine, chlorine or bromine atom.

An alkyl group, as such or in a group, for instance, an alkoxy, haloalkoxy or alkoxycarbonyl group, may have, for example, from 1 to 10 carbon atoms, for instance from 1 to 6 carbon atoms such as methyl, ethyl, propyl, butyl, 2-methylbutyl and pentyl.

An aryl group may be, for example, a phenyl group.

A cycloalkyl or cycloalkenyl group may have, for example from 3 to 6 carbon atoms, such as cyclopropyl, cyclopentyl, cyclohexyl, or cyclopentenyl.

An acyl group may be, for example, an alkanoyl group such as acetyl.

A heteroaryl group may be, for example, a 5- or 60-membered aromatic, heterocyclic ring containing one or more nitrogen, oxygen or sulphur atoms, for instance pyridyl, pyrimidyl, imidazolyl, tetrazolyl, pyridyl, thiophenyl or furyl.

An aralkyl group may be, for example, a benzyl group.

An alkenyl or alkynyl group may have, for example, from 2 to 10 carbon atoms, for instance 2 to 6 carbon atoms such as ethenyl, propenyl or propynyl.

A carbamoyl group may be, for example, an aminocarbonyl group, an alkylaminocarbonyl group or a dialkylaminocarbonyl group, which alkyl groups may carry one or more halogen substituents such as fluorine, for example as in 2-methyl-4,4,4-trifluorobutylaminocarbonyl.

The alkylating agent used in the process according to the invention may be any organic compound having a saturated carbon atom attached to a leaving atom or group. Preferably it is a halide, for example a bromide or iodide, or an optionally substituted hydrocarbylsulphonyloxy ester, for example a p-toluenesulphonyloxy, p-bromophenylsulphonyloxy, methanesulphonyloxy or trifluoromethanesulphonyloxy ester. Most preferably it is a halide.

The organic residue of the alkylating agent may be, for example, an optionally substituted alkyl, alkenyl, alkynyl, cycloalkyl or cycloalkenyl group.

An optionally substituted alkyl, alkenyl, alkynyl, cycloalkyl or cycloalkenyl group may carry one or more substituents provided that none of these interfere with any of the steps in the process according to the invention. For example it may be substituted by one or more substituents selected from a halogen atom, an alkyl group, a cycloalkyl group, an alkoxycarbonyl group, an aralkyloxycarbonyl group, an alkanoyl group, an alkanoylamino group, an aralkylamino group, a carbamoyl group, or a phenyl group which may carry one or more substituents selected from a halogen atom, an alkyl group, an alkoxy group, an alkoxycarbonyl group, an N-arylsulphonylaminocarbonyl group, a carboxy group, an aralkyloxycarbonyl group, an alkanoylamino group or an aralkylamino group.

In our initial British Patent Application number 8927981.4, filed on 11th Dec., 1989, the compound 4-[5-(N-[4,4,4-trifluoro-2-methylbutyl]carbamoyl)-1- methylindol-3-ylmethyl]-3-methoxy-N-o-tolylsulphonylbenzamide is disclosed. This compound has the formula I (formula set out hereinafter). This compound has been found to antagonise the action of one or more of the arachidonic acid metabolites known as leukotrienes. It is useful wherever such antagonism is required. Thus, it may be of value in the treatment of those diseases in which leukotrienes are implicated, for example, in the treatment of allergic or inflammatory diseases, or of endotoxic or traumatic shock conditions.

The compound of formula I is preferably in the substantially pure (R)-form.

The compound of formula I may be prepared by acylating 2-methyl-4,4,4-trifluorobutylamine of formula II (formula set out hereinafter) or an acid addition salt thereof such as the hydrochloride with a carboxylic acid of formula III wherein U is carboxy or a reactive derivative thereof. The acylation is conveniently performed in the presence of a dehydrating agent, such as 1-(3-dimethylaminopropyl)-3-ethyl carbodiimide hydrochloride, optionally together with an organic base, for example, 4-dimethylaminopyridine.

The compound of formula III may be prepared from a compound of formula VI (formula set out hereinafter) in which T is COOR$^h$, U is COOR$^j$, and R$^h$ and R$^j$ are each independently a conveniently removed acid protecting group, for example phenyl, benzyl, or (1–6C)alkyl optionally bearing an acetoxy, (1–4C)alkoxy or (1–4C)alkylthio substituent. Particular values for R$^h$ and R$^j$ are, for example, methyl, ethyl, propyl, t-butyl, acetoxymethyl, methoxymethyl, 2-methoxyethyl, methylthiomethyl, phenyl or benzyl.

Thus a compound of formula VI may be converted into a corresponding compound of formula VII (formula set out hereinafter) by reaction with a conventional methylating agent, for example methyl iodide or dimethylsulphate.

The compound of formula VII may then be converted into another compound of formula VII in which T represents a carboxy group by selective conversion of the group COOR$^h$, for example by treatment with an alkali metal hydroxide such as sodium hydroxide or lithium hydroxide and water.

The compound of formula VII in which T represents a carboxy group may then be converted into a compound of formula VII in which T represents COCl by reaction with a chlorinating agent, for example thionyl chloride.

The compound of formula VII in which T represents COCl may then be reacted with 2-methylbenzenesulphonamide to afford a compound of formula III in which U is COOR$^j$ or a salt thereof.

The compound of formula III in which U is COOR$^j$ may then be converted into a compound of formula III in which U is a carboxy group by decomposing the ester group COOR$^j$, for example by treatment with sodium hydroxide and water.

The compound of formula II may be prepared in racemic form or in the form of a substantially pure enantiomer, for example the (R)-enantiomer.

The compound of formula II in racemic form may be prepared from 2-methyl-4,4,4-trifluorobutyric acid, or a reactive derivative thereof such as the hydrochloride, by reaction with ammonia followed by reduction of the resultant amide, for example using lithium aluminium hydride.

The compound of formula II in the form of the substantially pure (R)-enantiomer may be prepared from 4,4,4-trifluorobutyric acid as follows.

4,4,4-Trifluorobutyric acid may be converted into 4,4,4-trifluorobutyryl chloride by treatment with oxalyl chloride. The 4,4,4-trifluorobutyryl chloride may then be converted into (4R,5S)-4-methyl-3-(4,4,4-trifluorobutyryl)-5-phenyl-2-oxazolidinone by reaction with (4R,5S)-(+)-4-methyl-5-phenyl-2-oxazolidinone in the presence of butyl lithium. The product of this reaction may then be methylated by treatment with sodium bis(trimethylsilylamide) followed by methyl iodide to afford (4R,5S)-4-methyl-3-((2R)-2-methyl-4,4,4-trifluorobutyryl)-5-phenyl-2-oxazolidinone. This product may then be treated with lithium aluminium hydride to afford (R)-2-methyl-4,4,4-trifluorobutan-1-ol. Treatment of this alcohol with phthalimide in the presence of triphenylphosphine and diethyl azodicarboxylate affords (R)-2-(2-methyl-4,4,4-trifluorobutyl)-1H-isoindol-1,3(2H)-dione. Treatment of this product with hydrazine monohydrate followed by hydrochloric acid affords the desired (R)-2-methyl-4,4,4-trifluorobutylamine as the hydrochloride salt.

As stated previously, the compound of formula I possesses leukotriene antagonist properties. Thus, it antagonises at least one of the actions of one or more of the arachidonic acid metabolites known as leukotrienes, for example, $C_4$, $D_4$ and/or $E_4$, which are known to be powerful spasmogens (particularly in the lung), to increase vascular permeability and to be implicated in the pathogenesis of asthma and inflammation, as well as of endotoxic shock and traumatic shock. The compound of formula I is thus useful in treatment of diseases in which leukotrienes are implicated and in which antagonism of their action is desired. Such diseases include, for example, allergic pulmonary disorder such as asthma, hay fever and allergic rhinitis and certain inflammatory diseases such as bronchitis, ectopic and atopic eczema, and psoriasis, as well as vasospastic cardiovascular disease, and endotoxic and traumatic shock conditions.

The compound of formula I is a potent leukotriene antagonist and is useful whenever such activity is desired. For example, the compound of formula I is of value as a pharmacological standard for the development and standardisation of new dissase models and assays for use in developing new therapeutic agents for treating the diseases in which the leukotrienes are implicated.

When used in the treatment of one or more of the above mentioned diseases, the compound of formula I is generally administered as an appropriate pharmaceutical composition which comprises the compound of formula I as defined hereinbefore together with a pharmaceutically acceptable diluent or carrier, the composition being adapted for the particular route of administration chose. Such compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; in the form of aerosols or nebuliser solutions or suspension for administration by inhalation; and in the form of powders together with pharmaceutically acceptable inert solid diluents such as lactose for administration by insufflation. If a solid form of a compound of formula I is required, it may be preferred to use an amorphous form, which amorphous form may be prepared by adding an aqueous acid, for example hydrochloric acid, to a solution of the sodium salt of the compound of formula I in an alcohol-water mixture, for example methanol-water mixture, to precipitate the compound of formula I.

For oral administration a tablet or capsule containing up to 250 mg (and typically 5 to 100 mg) of the compound of formula I may conveniently be used. Similarly, for intravenous or intramuscular injection or infusion a sterile solution or suspension containing up to 10% w/w (and typically 0.05 to 5% w/w) of the compound of formula I may conveniently be used.

The dose of the compound of formula I to be administered will necessarily be varied according to principles well known in the art taking account of the route of administration and the severity of the conditions and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received.

The leukotriene antagonist properties of the compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436) and is also described in European Patent Application publication number 220,066 and in U.S. Pat. No. 4,859,692.

The selectivity of action of compounds as leukotriene antagonists as opposed to non-specific smooth muscle depressants may be shown by carrying out the above in vitro procedure using the non-specific spasmogen barium chloride at a concentration of $1.5 \times 10^{-3}M$, again in the presence of indomethacin at $5 \times 10^{-6}M$.

Alternatively, the antagonistic properties of the compound of formula I can be demonstrated in vitro by a receptor-ligand binding assay described by Aharony (Fed. Proc., 1987, 46, 691).

In general, the compound of formula I tested demonstrated statistically significant activity as $LTC_4$, $LTD_4$ and/or $LTE_4$ antagonists in one of the above tests at a concentration of about $10^{-8}M$ or much less. For example, a pKi value of 9.4 was typically determined for a compound of formula I substantially in the form of the (R)-enantiomer.

Activity as a leukotriene antagonist may also be demonstrated in vivo in laboratory animals, for example, in a routine guinea-pig aerosol test described in Snyder, et al. (*J. Pharmacol. Methods.*, 1988, 19, 219). In this test the particularly useful leukotriene antagonist properties of the carbamoyl derivative of formula I may be demonstrated. According to this procedure, guinea-pigs are pre-dosed with test compound as a solution in poly-(ethylene glycol) (generally 1 hour) before an aerosol challenge of leukotriene $LTD_4$ (starting with 2 ml of a 30 microgram/ml solution) and the effect of the test compound on the average time of leukotriene initiated change in breathing pattern (such as onset of dyspnea) recorded and compared with that in undosed, control guinea-pigs. Percent protection engendered by a test compound was calculated from the time delay to the onset of dyspnea compared to that for control animals. Typically, an $ED_{50}$ of 1.1 μmol/kg for a compound of formula I substantially in the form of the (R)-enantiomer following oral administration was determined, without any indication of untoward side-effects at several multiples of the minimum effective dose. By way of comparison, an oral $ED_{50}$ of 19.2 μmol/kg was measured for the compound of Example 10 of European Patent Application publication number 220,066.

According to a preferred aspect, therefore, the invention provides a process for the preparation of a 3alkylated indole of formula VI (formula set out hereinafter) in which U is $COOR^j$ and T is $COOR^h$ wherein $R^h$ and $R^j$ are each independently a conveniently removed acid protecting group, for example, phenyl, benzyl, or (1–6C)alkyl optionally bearing an acetoxy, (1–4C)alkoxy or (1–4C)alkylthio substituent. Particular values for $R^h$ and $R^j$ are, for example, methyl, ethyl, propyl, t-butyl, acetoxymethyl, methoxymethyl, 2-methoxyethyl, methylthiomethyl, phenyl, or benzyl.

The 3-alkylated indoles of formula VI may be obtained by the process according to the invention by selecting as the N-(2-nitrostyryl) enamine a compound of formula IV (formula set out hereinafter) wherein U has any of the meanings given above and each R independently represents a (1–4C)alkyl group or together represent a 4- or 5-membered alkylene or heteroalkylene chain, and as the alkylating agent, a compound of formula V (formula set out hereinafter) wherein T has any of the meanings given above and X is a leaving atom or group.

The reaction between the N-(2-nitrostyryl) enamine and the alkylating agent is conveniently effected at a temperature in the range of from 0° to 120° C., preferably from 15° to 80° C. Suitable solvents for the reaction include nitriles such as acetonitrile; halogenated hydrocarbons such as methylene chloride; ethers such as tetrahydrofuran; hydrocarbons such as toluene; esters such as ethyl acetate; and amides such as dimethylformamide or dimethylacetamide.

The product of the alkylation reaction is an imine salt. This salt is conveniently reacted with water directly, without isolation. The reaction is conveniently effected at a temperature in the range of from 0° to 100° C., preferably from 15° to 35° C. Suitable solvents for the reaction include those listed above for the alkylation reaction.

The reaction of the imine salt with water affords a (2-nitrophenyl)acetaldehyde.

According to another aspect, the invention provides a (2-nitrophenyl)acetaldehyde of formula VIII (formula set out hereinafter) wherein U and T have the meanings given above. The (2-nitrophenyl)acetaldehydes of formula VIII are useful as intermediates in the preparation of the aforementioned leukotriene antagonist, 4-[5-(N-[4,4,4-trifluoro-2-methylbutyl]carbamoyl)-1-methylindol-3-ylmethyl]-3-methoxy-N-o-tolylsulphonylbenzamide.

The (2-nitrophenyl)acetaldehyde is converted into the desired indole by reaction with a reducing agent capable of selectively reducing the nitro group; that is a reagent which reduces the nitro group but not the aldehyde group. Other substituentes in the (2-nitrophenyl)acetaldehyde for example nitro groups, may also be reduced.

Suitable reducing agents include, for example, iron in the presence of an acid e.g. an inorganic acid such as hydrochloric acid or a carboxylic acid such as acetic acid or propanoic acid; stannous chloride; titanium trichloride; sodium dithionite; hydrazine with Raney nickel; and hydrogen in the presence of a transition metal hydrogenation catalyst such as palladium or Raney nickel. Surprisingly good results have been obtained using iron in the presence of an acid, such as acetic acid.

The reduction is conveniently effected at a temperature in the range of from 0° to 120° C., preferably from 15° to 100° C. Suitable solvents include aromatic hydrocarbons such as toluene, benzene and the xylenes; ethers such as tetrahydrofuran; alcohols such as ethanol; water and esters such as ethyl acetate. When using iron in the presence of acetic acid, an excess of acetic acid may conveniently be used as solvent.

The N-(2-nitrostyryl) enamine starting material may be prepared from a 2-nitrotoluene according to the method described in U.S. Pat. No. 3,979,410 or Organic Synthesis, Volume 63, 1985, pages 214 to 225. For example, it may be prepared by reacting a 2-nitrotoluene with dimethylformamide dimethyl acetal. The reaction is preferably performed in the presence of pyrrolidine, in which case the N-(2-nitrostyryl) enamine product is a mixture of a (2-nitrostyryl) dimethylamine and a (2-nitrostyryl)pyrrolidine.

As stated hereinbefore, the process according to the present invention, and the novel intermediates of formula VIII are particularly useful in the preparation of the compound of formula I. According to a further aspect therefore, the invention provides the use of a (2-nitrophenyl)acetaldehyde of formula VIII in the preparation of 4-[5-(N-[4,4,4-trifluoro-2-methylbutyl]-carbamoyl)-1-methylindol-3-ylmethyl]-3-methoxy-N-o-tolylsulphonyl-benzamide.

The invention also provides a process for the preparation of 4-[5-(N-[4,4,4-trifluoro-2-methylbutyl]carbamoyl)-1-methylindol-3-yl-methyl]-3-methoxy-N-o-tolylsulphonylbenzamide, which comprises a) reacting a compound of formula V with a compound of formula IV, wherein each R independently represents a (1-4C)alkyl group or together represent a 4- or 5-membered alkylene or heteroalkylene chain, X is a leaving atom or group, T is COOR$^h$, U is COOR$^j$, and R$^h$ and R$^j$ are each independently a conveniently removed acid protecting group, to afford an imine salt, b) reacting the imine salt with water to afford a (2-nitrophenyl)acetaldehyde of formula VIII, c) reacting the (2-nitrophenyl)acetaldehyde of formula VIII with a reducing agent capable of selectively reducing the nitro group, to afford a compound of formula VI, d) methylating the compound of formula VI to afford a compound of formula VII, e) converting the group T into a 2-methylbenzenesulphonamidocarbonyl group by removing the protecting group R$^h$, and reacting the resultant carboxylic acid or a reactive derivative thereof with 2-methylbenzenesulphonamide or a salt thereof, and f) converting the group U into a 2-methyl-4,4,4-trifluorobutylaminocarbonyl group by removing the protecting group R$^j$, and reacting the resultant carboxylic acid or a reactive derivative thereof with 2-methyl-4,4,4-trifluorobutylamine or an acid addition salt thereof.

It will be appreciated that the steps e) and f) can be carried out in the order stated or in the reverse order.

The following non-limiting Examples illustrate the invention.

Notes: NMR data is in the form of delta values, given in parts per million relative to tetramethylsilane as internal standard. Kieselgel is a trade mark of E Merck, Darmstadt, Germany. Yields are for illustration only and are not to be construed as the maximum attainable after conventional process development. Unless otherwise stated, procedures were carried out at ambient temperature and pressure.

EXAMPLE 1

Preparation of Methyl 4-(5-methoxycarbonylindol-3-ylmethyl)-3-methoxybenzoate a) Methyl 3-methyl-4-nitrobenzoate To a stirred suspension of 3-methyl-4-nitrobenzoic acid (100 g, 0.55 mole) in methanol (400 ml) was added thionyl chloride (36 g, 0.30 mole), over a period of 1 hour (the temperature of the reaction mixture rising to about 35°-40° C.). The mixture was heated to reflux for 1.5 hours, then cooled to 50°-55° C. and maintained at this temperature for 30 minutes prior to cooling to ambient temperature. Water (100 ml) was added over 30 minutes, with cooling applied to maintain the temperature at 20°-25° C. Filtration was followed by washing of the solid with water (2×100 ml), and drying at 40° C. under vacuum, to afford 103 g (95%) of methyl 3-methyl-4-nitrobenzoate as a yellow solid; m.p. 83°-85° C.; NMR (250 MHz, CDCl$_3$), 2.62 (s, 3H, ArCH$_3$), 3.98 (s, 3H, CO$_2$CH$_3$), 8.01 (m, 3H).

b) 5-Methoxycarbonyl-2-nitro-β-(1-pyrrolidinyl)styrene and 5-methoxycarbonyl-2-nitro-β-(dimethylamino)styrene A mixture of the product of step a) (100 g, 5.13 mole), N,N-dimethylformamide dimethyl acetal (1219 g, 10.26 mole) and pyrrolidine (382 g, 5.38 mole) in N,N-dimethylformamide (3000 ml) was heated to reflux over about 45 minutes, and maintained at a gentle reflux for 2.5 hours. After cooling the reaction mixture to ambient temperature, it was added over 20 minutes to 10 l of ice/water. The resulting slurry was stirred for 30 minutes prior to filtration and washing of the solid with cold water (3×1500 ml). Drying at 50° C. under vacuum afforded 1208 g (83.3%) of an 82:18 mixture of 5-methoxycarbonyl-2-nitro-β-(1-pyrrolidinyl)styrene and 5-methoxycarbonyl-2-nitro-β-(1-dimethylamino)styrene as a dark red solid; m.p. 109°-112° C.; NMR (250 MHz, CDCl$_3$), 1.97 (m, 0.82×4H), 2.95 (s, 0.18×6H, N(CH$_3$)$_2$), 3.37 (m, 0.82×4H), 3.93 (s, 3H, CO$_2$CH$_3$), 5.77 (d, 0.82×1H), 5.78 (d, 0.18×1H), 7.08 (d, 0.18×1H), 7.39 (d, 0.82×1H), 7.49 (dd, 0.82×1H), 7.53 (dd, 0.18×1H), 7.82 (d, 1H), 8.13 (m, 1H).

c) 2-(5-methoxycarbonyl-2-nitro)phenyl-2-(2-methoxy-4-methoxycarbonyl)benzylacetaldehyde The product of step b) (800 g, 2.95 mole) and methyl 4-bromomethyl-3-methoxybenzoate (770 g, 2.97 mole) in acetonitrile (2000 ml) were heated to reflux over 20 minutes and held at this temperature for 50 minutes. More benzoate (35 g, 0.135 mole) was then added and heating continued for a total of 4 hours. After cooling to ambient temperature, the mixture was diluted with water (2000 ml), added over 5 minutes, during which time a dark brown solid precipitated. The mixture was stirred for 30 minutes and filtered, the precipitate being washed with acetonitrile (500 ml), and dried at 45° C. under vacuum. This afforded 2-(5-methoxycarbonyl-2- nitro)phenyl-2-(2-methoxy-4-methoxycarbonyl)benzylacetaldehyde as a pale brown solid, 914.5 g (77.3%); m.p. 117°–120° C.; NMR (250 MHz, CDCl$_3$): 3.11 (dd, 1H), 3.50 (dd, 1H), 3.82, 3.90, 3.97 (each s, 3H, OCH$_3$ plus 2×CO$_2$CH$_3$), 4.65 (dd, 1H), 7.00 (d, 1H), 7.46 (m, 2H), 7.88 (d, 1H), 7.93 (d, 1H), 8.04 (dd, 1H), 9.82 (s, 1H).

d) Methyl 4-(5-methoxycarbonylindol-3-ylmethyl)-3-methoxybenzoate

A stirred suspension of the product of step c) (600 g, 1.49 mole) and iron powder (600 g, 10.7 mole) in acetic acid (2.2 l) and toluene (3.8 l), was heated carefully to reflux. An exotherm occurred at 95° C., resulting in the mixture reaching reflux without external heating. Heating was then applied as necessary to maintain reflux for a total of 2 hours. The mixture was allowed to cool to ambient temperature, and then cooled at 5° C. for 30 minutes prior to filtration and washing of the solid with toluene (2×200 ml). The combined filtrates and washings were washed with 15% brine (3.8 l) and 5% sodium bicarbonate solution (3.8 l), and evaporated under reduced pressure. The resulting solid was recrystallised from methanol (2 l) to afford methyl 4-(5-methoxycarbonylindol-3-ylmethyl)-3-methoxybenzoate (420 g, 79.9%), m.p. 136°–138° C.; NMR (250 MHz, CDCl$_3$): 3.88, 3.90, 3.92 (each s, 3H, OCH$_3$ plus 2×CO$_2$CH$_3$), 4.16 (s, 2H, ArCH$_2$Ar′), 6.98 (d, 1H), 7.12 (d, 1H), 7.33 (d, 1H), 7.52 (m, 2H), 7.89 (dd, 1H), 8.30 (br.s, 1H), 8.36 (d, 1H).

COMPARATIVE EXAMPLE

Preparation of Methyl 4-(5-benzyloxycarbonylindol-3-ylmethyl)-3-methoxybenzoate by alkylation of benzyl indole-5-carboxylate.

A solution of benzyl indole-5-carboxylate (86.8 g), methyl 4-bromomethyl-3-methoxybenzoate (89.5 g) and potassium iodide (57.4 g) in N,N-dimethylformamide (900 ml) was heated to 80° C. for 10 hours. The reaction mixture was evaporated and partitioned between diethyl ether and water. The organic layer was separated and washed with water. The aqueous washes were combined and extracted with diethyl ether. The combined organic extract was dried (MgSO$_4$) and evaporated. The residue was purified by flash chromatography, eluting sequentially with 0:1:1, 2:48:50, 4:46:50, 5:45:50, and 10:40:50 ethyl acetate:hexane:methylene chloride, to afford methyl 4-iodomethyl-3-methoxybenzoate (27.8 g), recovered benzyl indole-5-carboxylate (29.6 g), and the crude product as a tan solid (50.6 g). Treatment of the recovered benzyl indole-5-carboxylate (29.6 g) in N,N-dimethylformamide (250 ml) with methyl 4-iodomethyl-3-methoxybenzoate (29.8 g) at 80° C. for 12 hours, followed by evaporation, gave a dark residue, which was dissolved in diethyl ether and washed with water (3 times). The aqueous washes were combined and extracted with diethyl ether. The combined organic extract was dried (MgSO$_4$) and evaporated. The residue was purified by flash chromatography, eluting sequentially with 0:1:1, 2:48:50, 5:45:50, and 10:40:50 ethyl acetate:hexane:methylene chloride, to give further crude product as a tan solid (31.9 g). The combined crude product (82.5 g) was suspended in diethyl ether (400 ml), heated to reflux for 30 min, cooled and filtered to obtain methyl 4-(5-benzyloxycarbonylindol-3-ylmethyl)-3-methoxybenzoate as an ivory solid (46.1 g, 31%); partial NMR (250 MHz, CDCl$_3$): 3.84 (s, 3H, CO$_2$CH$_3$), 3.88 (s, 3H, OCH$_3$), 4.14 (s, 2H, CH$_2$), 5.35 (s, 2H, OCH$_2$), 6.97 (d, 1H, indole-H(2)), 8.15 (br, 1H, NH), 8.37 (s, 1H, indole-H(4)).

This Comparative Example demonstrates the lower yield of 3-alkylated product obtainable by direct alkylation of an indole compared with that obtainable by the process according to the invention.

EXAMPLE 2

Preparation of Methyl 3-benzylindole-5-carboxylate a) 2-(5-Methoxycarbonyl-2-nitro)phenyl-2-benzylacetaldehyde

The product of Example 1b) (5.42 g, 20 mmole) and benzyl bromide (2.39 ml, 20 mmole) in acetonitrile (15 ml) were heated at reflux under an atmosphere of nitrogen for 5 hours. Water (2 ml) was added and the solution was then concentrated in vacuo. The residue was passed through a silica column (50 Kieselgel 60), with dichloromethane (300 ml) as eluant. Concentration in vacuo gave the intermediate aldehyde as a dark oil, 5.8 g; NMR (250 MHz, CDCl3): 3.11 (dd, 1H), 3.57 (dd, 1H), 3.97 (s, 3H, OCH3), 4.56 (dd, 1H), 7.03–7.40 (m, 5H, Ph), 7.95 (m, 2H), 8.10 (dd, 1H), 9.82 (s, 1H, CHO).

b) Methyl 3-benzylindole-5-carboxylate

The product of step a) (5.8 g) was heated in toluene (40 ml) and acetic acid (26.4 ml) with iron powder (5.17 g, 92.7 mmole), at 95° C. under an atmosphere of nitrogen for 3.5 hours. After cooling overnight, the solid was removed by filtration and washed with toluene (2×20 ml). The combined filtrate and washings were washed with 15% brine (40 ml) and saturated aqueous sodium bicarbonate (40 ml), and concentrated in vacuo. The residue was passed through a silica column (35 g Kieselgel 60), with dichloromethane (100 ml) as eluant, and the eluate concentrated in vacuo. Crystallisation of the residue from toluene (15 ml) gave 2.65 g (50% overall from the enamine) of methyl 3-benzylindole-5-carboxylate; NMR (250 MHz, CDCl3): 3.91 (s, 3H, OCH3), 4.14 (s, 2H, ArCH2Ar′), 6.92 (d, 1H), 7.15–7.36 (m, 6H), 7.90 (dd, 1H), 8.25 (br.s, 1H, NH), 8.32 (s, 1H); microanalysis found: C, 76.8; H, 5.6; N, 5.1%; C17H15NO2 requires: C, 77.0; H, 5.7; N, 5.3%.

EXAMPLE 3

Preparation of Methyl 3-(3-methylbut-2-enyl)indole-5-carboxylate a) 2-(5-Methoxycarbonyl-2-nitro)phenyl-2-(3-methyl-but-2-enyl)acetaldehyde

The product of Example 1b) (5.42 g, 20 mmole) and 1-bromo-3-methylbut-2-ene (2.33 ml, 20 mmole) in acetonitrile (15 ml) was stirred overnight at ambient temperature, followed by heating to 50° C. for one hour. The solution was then worked up as in Example 2 to yield 2-(5-methoxycarbonyl-2-nitro)phenyl-2-(3-methyl-but-2-enyl)acetaldehyde as a dark red oil, 5.46 g; NMR (250 MHz, CDCl3): 1.51 (s, 3H, CCH3), 1.63 (s, 3H, CCH3), 2.57 (m, 1H), 2.90 (m, 1H), 3.97 (s, 3H, OCH3), 4.24 (m, 1H), 5.04 (m, 1H, C=CH), 8.00 (m, 2H), 8.11 (dd, 1H), 9.82 (s, 1H, CHO).

b) Methyl 3-(3-methylbut-2-enyl)indole-5-carboxylate

The product of step a) was reduced following the method described in Example 2b) to afford a yellow oil which crystallised on standing. Recrystallisation from cyclohexane (20 ml) afforded 3.14 g (64.6% overall from the enamine) of methyl 3-(3-methylbut-2-enyl)indole-5-carboxylate, m.p. 88°–91° C.; NMR (250 MHz, CDCl3): 1.78 (s, 6H, C(CH3)2), 3.48 (d, 2H, ArCH2), 3.95 (s, 3H, OCH3), 5.43 (m, 1H, C=CH), 7.00 (s, 1H), 7.33 (d, 1H), 7.90 (dd, 1H), 8.22 (br.s, 1H, NH), 8.38 (s, 1H); microanalysis found: C, 74.1; H, 7.2; N, 5.8%. C15H17NO2 requires: C, 74.0; H, 7.0; N, 5.8%.

EXAMPLE 4

Preparation of methyl 3-methoxycarbonylmethylindole-5-carboxylate a)
2-(5-Methoxycarbonyl-2-nitro)phenyl-2-methoxycarbonylmethylacetaldehyde

The product of Example 1b) (5.42 g, 20 mmole), methyl bromoacetate (1.89 ml, 20 mmole) and sodium iodide (3.00 g, 20 mmole) in acetonitrile (15 ml) was heated at 65° C. under an atmosphere of nitrogen for 24 hours. The cooled mixture was treated with water (3 ml), concentrated in vacuo and partitioned between water (50 ml) and ethyl acetate (50 ml). The organic layer was washed with 10% aqueous sodium sulfite (50 ml) and concentrated in vacuo. Chromatography on silica (200 g Kieselgel 60), eluted with 1000 ml dichloromethane afforded 2-(5-methoxycarbonyl-2-nitro)phenyl-2-methoxycarbonylmethylacetaldehyde as a red gum, 2.35 g; NMR (250 MHz, CDCl3): 2.80 (dd, 1H), 3.30 (dd, 1H), 3.69 (s, 3H, OCH3), 3.97 (s, 3H, OCH3), 4.70 (t, 1H), 7.96 (d, 1H), 8.06 (d, 1H), 8.17 (dd, 1H), 9.78 (s, 1H, CHO).

b)
Methyl-3-methoxycarbonylmethylindole-5-carboxylate

The product of step a) was reduced following the method described in Example 2b) to afford a dark solid. Recrystallisation from dichloromethane-toluene (15 ml) gave 1.24 g (25.6% overall from the enamine) of methyl 3-methoxycarbonylmethylindole-5-carboxylate, m.p. 131°–133° C.; NMR (250 MHz, CDCl3): 3.73 (s, 3H, OCH3), 3.81 (s, 2H, ArCH2), 3.95 (s, 3H, OCH3), 7.20 (d, 1H), 7.32 (d, 1H), 7.90 (dd, 1H), 8.37 (s, 1H), 8.50 (br.s, 1H, NH); microanalysis found: C, 63.0; H, 5.3; N, 5.6%. C13H13NO4 requires: C, 63.2; H, 5.3; N, 5.7%.

EXAMPLE 5

Preparation of (R)-4-[5-(N-[4,4,4-trifluoro-2-methylbutyl]carbamoyl)-1-methylindol-3-yl-methyl]-3-methoxy-N-o-tolylsulphonylbenzamide a) Methyl 4-(5-methoxycarbonyl-1-methylindol-3-ylmethyl)-3-methoxybenzoate

To a stirred solution of the product of Example 1d) (50 g, 142 mmole) and methyl iodide (87.5 ml, 1.42 mole) in tetrahydrofuran (333 ml) was added concentrated sodium hydroxide liquor (40 ml, 0.71 mole). After 7.5 hours water (200 ml) was added, and the organic layer separated and washed with brine (150 ml) and finally water (150 ml). After removal of 300 ml distillate under reduced pressure, a solid precipitated which was collected by filtration and washed with hexane (50 ml). Drying of the beige solid at 40° C. under vacuum afforded 48.0 g (91.3%) of methyl 4-(5-methoxycarbonyl-1-methylindol-3-ylmethyl)-3-methoxybenzoate, m.p. 137°–140° C.; NMR (250 MHz, DMSO-d6): 3.91 (s, 3H, N-CH3), 3.98 (s, 6H, 2×CO2CH3), 4.07 (s, 3H, OCH3), 4.22 (s, 2H, ArCH2Ar'), 7.34 (m, 2H), 7.61 (m, 3H), 7.90 (dd, 1H), 8.33 (d, 1H).

b)
4-(5-Methoxycarbonyl-1-methylindol-3-ylmethyl)-3-methoxybenzoic acid.

To a solution of the product of step a) (33.50 g, 91.3 mmole) in tetrahydrofuran (335 ml) and methanol (100 ml) was added water (67 ml) and lithium hydroxide monohydrate (4.025 g, 95.8 mmole). After the reaction mixture had stirred at ambient temperature for about 20 hours, it was heated to reflux and about 250 ml distillate collected. The residual solution was cooled to room temperature, diluted with water (210 ml) and toluene (210 ml), and the organic layer separated and extracted with water (40 ml). Combined aqueous layers were treated dropwise with acetic acid (4.18 ml, 73.0 mmole) and stirred for around 30 minutes prior to collection of the precipitate by filtration. After washing with water (2×67 ml) and methanol (2×67 ml), 28.07 g (84.1%) of 4-(5-methoxycarbonyl-1-methylindol-3-ylmethyl)-3-methoxybenzoic acid were obtained as a white solid, m.p. 228°–230° C.; NMR (250 MHz, DMSO-d6): 3.77, 3.83, 3.93 (each s, 3H, OCH3 plus NCH3 plus CO2CH3), 4.08 (s, 2H, ArCH2Ar'), 7.17 (d, 1H), 7.23 (s, 1H), 7.49 (m, 3H), 7.77 (dd, 1H), 8.21 (d, 1H).

c)
4-(5-Methoxycarbonyl-1-methylindol-3-ylmethyl)-3-methoxybenzoyl chloride

A solution of thionyl chloride (2.42 ml, 33 mmole) in dichloromethane (10 ml) was added dropwise over 5 minutes to a suspension of the product of step b) (10.59 g, 30 mmole) in dichloromethane (90 ml) containing N,N-dimethylformamide (0.2 ml), stirred at reflux under an atmosphere of nitrogen. After 2 hours, solvent was removed from the resulting yellow solution by distillation, approximately 85 ml distillate being collected. Dilution of the residue with methyl t-butyl ether was followed by stirring at 15° C. for 30 minutes prior to collection of the solid precipitate by filtration. After washing with methyl t-butyl ether (2×20 ml), 4-(5-methoxycarbonyl-1-methylindol-3-ylmethyl)-3-methoxybenzoyl chloride was obtained as an off-white solid, 10.10 g (90.6%); m.p. 147°–149° C.; NMR (250 MHz, DMSO-d6): 3.76, 3.92, 3.97 (each s, 3H, NCH3 plus OCH3 plus CO2CH3), 4.16 (s, 2H, ArCH2Ar'), 6.87 (s, 1H), 7.20 (d, 1H), 7.29 (d, 1H), 7.54 (d, 1H), 7.66 (dd, 1H), 7.92 (dd, 1H), 8.32 (d, 1H).

d)
4-(5-Methoxycarbonyl-1-methylindol-3-ylmethyl)-3-methoxy-N-(2-methylphenylsulfonyl)benzamide A solution of 4-(dimethylamino)pyridine (8.17 g, 66.9 mmole) in dichloromethane (20 ml) was added over 15 minutes to a stirred suspension of the product of step c) (9.94 g, 26.8 mmole) and 2-methylbenzenesulfonamide (6.87 g, 40.1 mmole) in dichloromethane (30 ml). After 45 minutes the solution was heated to reflux and 20 ml distillate collected. Acetone (150 ml) was added and a further 80 ml distillate collected. The mixture was allowed to cool overnight and finally stirred at 15° C. before collection of the solid by filtration. This was then slurry-washed with methanol (3×30 ml) to afford 16.22 g (96.4%) of 4-(5-methoxycarbonyl-1-methylindol-3-ylmethyl)-3-methoxy-N-(2-methylphenylsulfonyl)benzamide, as its 4-(dimethylamino)pyridine salt; m.p. 185°–187° C. (with partial melting and resolidification at 138°–140° C.); NMR (250 MHz, DMSO-d6): 2.53 (s, 3H, ArCH3), 3.13 (s, 6H, N(CH3)2), 3.76, 3.83, 3.86 (each s, 3H, OCH3 plus NCH3 plus CO2CH3), 4.02 (s, 2H, ArCH2Ar'), 6.92 (d, 2H), 7.02 (d, 1H), 7.11–7.32 (m, 4H), 7.39–7.53 (m, 3H), 7.75 (dd, 1H), 7.88 (d, 1H), 8.20 (m, 3H).

e) 4-(5-Carboxy-1-methylindol-3-ylmethyl)-3-methoxy-N-(2-methylphenylsulfonyl)benzamide A mixture of the product of step d) (15 g, 23.8 mmole), concentrated sodium hydroxide liquor (6.75 ml, 119 mmole), water (85 ml) and tetrahydrofuran (18 ml) was stirred for three hours at 65° C., and the now homogeneous solution cooled to 50°–55° C. and maintained at this temperature during the subsequent acidification and extraction. Concentrated hydrochloric acid was added to a pH of 7–8, followed by addition of tetrahydrofuran (44 ml) and n-butyl acetate (29 ml), and further adjustment of the pH to 1–2. The reaction mixture was allowed to settle and the lower aqueous layer separated. The organic layer was washed with 5% brine solution (2×20 ml). The tetrahydrofuran was removed by distillation (ca 40 ml distillate collected at a jacket temperature of 95° C.), and the residual mixture cooled to 15°–20° C. The product was collected by filtration, washed with butyl acetate (15 ml) and dried at 50° C. The yield of 4-(5-carboxy-1-methylindol-3-ylmethyl)-3-methoxy-N-(2-methylphenylsulfonyl)-benzamide was 11.08 g (94%); m.p. 264°–267° C.; NMR (250 MHz, DMSO-d6): 2.63 (s, 3H, ArCH3), 3.78 (s, 3H, NCH3), 3.95 (s, 3H, OCH3), 4.08 (s, 2H, ArCH2Ar'), 7.18 (d, 1H), 7.22 (s, 1H), 7.38–7.65 (m, 6H), 7.79 (d, 1H), 8.06 (d, 1H), 8.20 (s, 1H).

f) (R)-4-[5-(N-[4,4,4-trifluoro-2-methylbutyl]carbamoyl)-1-methylindol-3-ylmethyl]-3-methoxy-N-o-tolylsulphonylbenzamide To a mixture of 4-(5-carboxy-1-methylindol-3-ylmethyl)-3-methoxy-N-(2-methylphenylsulfonyl)benzamide (103.5 g), 4-dimethylaminopyridine (112.4 g), and 1-(3-dimethylaminopropyl)-3-ethylcarbodiimide hydrochloride (51.8 g) in tetrahydrofuran (distilled from sodium benzophenone ketyl) (2.0 L), which had been stirred for 2 hours, was added (R)-2-methyl-4,4,4-trifluorobutylamine hydrochloride (42.6 g); and the reaction mixture was stirred overnight (about 18 hours, incomplete reaction) then heated to reflux for two hours (complete reaction). The cooled reaction mixture was diluted with ethyl acetate (2 L) washed with 1N hydrochloric acid (twice) and brine, dried (MgSO4) and evaporated. The residue (138.6 g) was combined with impure product from similar procedures (28.0 g) and purified by flash chromatography, eluting with methylene chloride:ethyl acetate (sequentially, 1:0, 9:1 and 3:1) to afford a solid which was triturated twice with ether to give the crude title compound (135.2 g) which was recrystallized from ethanol (1.2 L) and acetone (0.3 L) (concentrated by boiling to about 0.9 L and refrigerated) and dried under vacuum to provide the title compound (117.1 g, 65% recovery) as a white crystalline solid; m.p. 141.5°–143.5° C.; NMR (300 MHz, DMSO-d6): 1.01 (d, 3H, CH3), 2.0–2.2 (m, 2H, CF3CH2), 2.3–2.5 (m, 1H, CHCH3), 2.61 (s, 3H, ArCH3), 3.23 (br t, 2H, CH2N), 3.76 (s, 3H, NCH3), 3.92 (s, 3H, OCH3), 4.07 (s, ArCH2Ar'), 7.13 (s, 1H), 7.17 (d, 2H), 7.38–7.69 (m, 6H), 7.72 (d, 1H), 8.05 (d, 1H), 8.11 (s, 1H), 8.46 (br t, 1H, NHCO); analysis for C31H32F3N3O5S: calculated: C, 60.48; H, 5.24; N, 6.83%, found: C, 60.47; H, 5.27; N, 6.67%

The starting amine hydrochloride was prepared as follows:

a. 4,4,4-Trifluorobutyric acid

A solution of lithium hydroxide monohydrate (324 g) in water (1.8 l) was added to a stirred solution of ethyl 4,4,4-trifluorobutyrate (436 g) in methanol (2.0 l) and dry tetrahydrofuran (2.0 l) and the suspension was stirred overnight. After the suspension was partially evaporated, the residue was diluted with water and washed with diethyl ether. The aqueous layer was acidified with 6M hydrochloric acid and extracted with diethyl ether. The combined extracts were washed (brine), dried (MgSO4), and filtered. The filtrate was evaporated and the residue distilled (b.p. 165°–168° C.) to give 4,4,4-trifluorobutyric acid (347 g, 95%); m.p. 27°–30° C.; partial NMR; (300 MHz, CDCl3): 2.33–2.57 (m, 2H, CF3CH2), 2.66 (t, CH2CO2H).

b. 4,4,4-Trifluorobutyryl chloride

Diethyl formamide (1.0 ml) and oxalylchloride (239 ml) were added to a 0° C. solution of 4,4,4-trifluorobutyric acid (343 g) in dry methylene chloride (230 ml) and warmed to room temperature overnight. The methylene chloride was removed by distillation and the residue distilled to yield 4,4,4-trifluorobutyryl chloride (328 g, 85%); bp 103°–106° C.; partial NMR (300 MHz, CDCl3): 2.47–2.64 (m, 2H, CF3CH2) 3.19 (t, H, CH2COCl).

c. (4R,5S)-4-Methyl-3-(4,4,4-trifluorobutyryl)-5-phenyl-2-oxazolidinone

A solution of n-butyllithium (2.0 mole) in hexane was added to a stirred solution of (4R,5S)-(+)-4-methyl-5-phenyl-2-oxazolidinone (353 g) in dry tetrahydrofuran (2500 ml) at −78° C. under an inert atmosphere. The solution was stirred at −70° c. for 15 min, then 4,4,4-trifluorobutyryl chloride (320 g) was added over 30 min at −60° C. and the mixture warmed to room temperature and stirred overnight. The mixture was evaporated and the residue was partitioned between diethyl ether and water. The ethereal layer was washed (1N hydrochloric acid, brine (twice)), dried (MgSO4), and evaporated to yield crude product (604 g, about 100%). Filtration through 3000 ml of silica gel using 1:1 methylene chloride:hexanes as the eluent afforded a white solid. Recrystallization from methylene chloride:hexanes afforded (4R,5S)-4-methyl-3-(4,4,4-trifluorobutyryl)-5-phenyl-2-oxazolidinone (519 g, 86%); m.p. 93°–95° C.; partial NMR (300 MHz, CDCl3): 0.91 (d, 3H, CH3), 2.45–2.65 (m, 2H, CF3CH2), 3.18–3.40 (m, 2H, CH2CO), 4.78 (m, 1H, 4-H oxazolidinone), 5.70 (d, 1H, 5-H oxazolidone), 7.30–7.44 (m, 5H, Ar).

d. (4R,5S)-4-methyl-3-((2R)-2-methyl-4,4,4-trifluorobutyryl)-5-phenyl-2-oxazolidinone To a stirred solution of sodium bis(trimethylsilylamide) (1.9 mole) in tetrahydrofuran (1900 ml) cooled to −40° C. was added a solution of (4R,5S)-4-methyl-3-(4,4,4-trifluorobutyryl-5-phenyl-2-oxazolidinone (517 g) in dry tetrahydrofuran (800 ml) under an inert atmosphere. The mixture was maintained at −40° C. for one-half hour, and warmed to −35° C. over an additional one-half hour. To this mixture was added iodomethane (142 ml) over approximately 15 min while maintaining the internal reaction temperature between −35° C. and −30° C. The mixture was stirred for an additional 2 h at −30° C. and the cold reaction mixture was poured over chilled aqueous ammonium chloride (700 g in 2 l water). The mixture was diluted with diethyl ether (1 l) and the layers separated. The organic layer was washed (25% w/v aqueous sodium bisulfate, brine). The aqueous portions were extracted with 1:1 methylene chloride:diethyl ether and methylene chloride. The combined organic layers were dried (MgSO$_4$) and evaporated to afford crude product (595 g) as reddish oil. Filtration through silica gel (3000 ml), using a gradient of 1–5% ethyl acetate in hexanes, followed by evaporation, afforded a white solid (490 g) which was a mixture of the named product, the diastereomeric methylated side product and unmethylated starting material. Crystallization from diethyl ether:hexanes afforded (4R,5S)-4-methyl-3-((2R)-2-methyl-4,4,4-trifluorobutyryl)-5-phenyl-2-oxazolidinone (370 g, 68%) as a white solid; m.p. 68°–70° C. Analysis by HPLC (Zorbax silica gel, 4.6 mm×25 cm, 1:9 ethyl acetate:hexanes, FR=1.5 ml/min, UV detector at 254 nm) showed this sample to be about 99% pure (retention volume=2.6). A second recrystallization of this white solid from diethyl ether:hexanes afforded an analytical sample of (4R,5S)-4-methyl-3-((2methyl-4,4,4-trifluorobutyryl)-5-phenyl-2-oxazolidinone (300 g, 55%) as transparent colourless needles; m.p. 74.5°–75° C.; partial NMR (300 MHz, CDCl$_3$): 0.89 (d, 3H, 4—CH$_3$ of oxazolidinone), 1.33 (d, 3H, CH(CH$_3$)CO), 2.10–2.31 (m, 1H, CF$_3$CH$_2$), 2.74–2.97 (m, 1H, CF$_3$CH$_2$), 4.03–4.17 (m, 1H, CHCO), 4.79 (m, 1H, 43-H of oxazolidinone), 5.71 (d, 1H, 5-H of oxazolidinone), 7.26–7.44 (m, 5H, phenyl).

HPLC analysis as above showed 99.9% purity; analysis for C$_{15}$H$_{16}$F$_3$NO$_3$: calculated: C, 57.14; H, 5.11; N, 4.44%, found: C, 57.17; H, 5.16; N, 4.59% e. (R)-2-Methyl-4,4,4-trifluorobutan-1-ol

Lithium aluminium hydride (10.26 g) was added to a stirred solution of (4R,5S)-4-methyl-3-((2R)-2-methyl-4,4,4-trifluorobutyryl)-5-phenyl-2-oxazolidinone (28 g) in dry diethyl ether (200 ml) at −20° C. under an inert atmosphere, then the mixture was warmed to 0° C. After 2 h at 0° C., water (10.27 ml), 10% w/v sodium hydroxide (10.27 ml) and water (31 ml) were added, and the mixture was stirred 20 min. The salts were filtered and washed with distilled diethyl ether. The diethyl ether solution was dried (K$_2$CO$_3$) and diluted with pentane. This resulted in precipitation of recovered (4R,5S)-(+)-4-methyl-5-phenyl-2-oxazolidinone which was isolated by filtration. Concentration of the filtrate by distillation afforded several fractions. The first fractions (bath temperature to 60° C.) were pentane and diethyl ether; a second set of fractions (bath temperature 60° C. to 100° C.) was 12 g of a oil that was a 40:60 mixture of (R)-2-methyl-4,4,4-trifluorobutane-1ol (calculated as 4.8 g alcohol) and diethyl ether by NMR.

Warming the remaining tarry residue (bath temperature 85° C.) under vacuum (13,330 Pa) afforded an additional 7.2 g of (R)-2-methyl-4,4,4-trifluorobutan-1ol (total yield, 12.0 g, 94%); partial NMR (300 MHz, CDCl$_3$-D$_2$O shake): 1.06 (d, 3H, CH$_3$), 1.41 (br t, 1H, OH), 1.86–2.07 (m, 2H, CH(CH$_3$) plus one CF$_3$CH$_2$), 2.31–2.42 (m, 1H, one CF$_3$CH$_2$), 3.49 (dd, 1H, one CH$_2$OH), 3.58 (dd, 1H, one CH$_2$OH). f. (R)-2-(2-Methyl-4,4,4-trifluorobutyl)-1H-isoindol-1,3(2H)-dione Diethyl azodicarboxylate (15.4 ml) was added to a 20 C., stirred slurry of (R)-2-methyl-4,4,4-trifluorobutan-1-ol (about 12.0 g), phthalimide (13.4 g), and triphenylphosphine (23.7 g) in diethyl ether (about 6.5 g, see above) and dry tetrahydrofuran (110 ml), warmed to room temperature overnight, and stirred an additional 8 h. The mixture was evaporated, methylene chloride was added to the residue, and the slurry was filtered. The filtrate was purified by flash chromatography, eluting with 1:1 methylene chloride:hexanes, to give (R)-2-(2-methyl-4,4,4-trifluorobutyl)-1H-isoindol-1,3(2H)-dione (17.1 g, 75%) as a white solid; m.p. 45°–47° C.; partial NMR (400 MHz, CDCl$_3$): 1.08 (d, 3H, CH$_3$), 1.94–2.07 (m, 1H, CF$_3$CH$_2$), 2.14–2.31 (m, 1H, CF$_3$CH$_2$), 2.36–2.50 (m, 1H, CHCH$_3$), 3.58 (dd, 1H, CH$_2$N), 3.64 (dd, 1H, CH$_2$N).

g. (R)-2-Methyl-4,4,4-trifluorobutylamine hydrochloride

Hydrazine monohydrate (3.1 ml) was added to a stirred solution of (R)-2-(2-methyl-4,4,4-trifluorobutyl)-1H-isoindole-1,3(2H)-dione (17.1 g) in anhydrous ethanol (85 mL) and heated to reflux. After three hours' reflux, the solution was cooled; ethanol (40 mL) was added; and the solution was acidified to pH 1 by addition of concentrated hydrochloric acid and was filtered. The filtrate was evaporated, and the residue was purified by sublimation (bath temperature 170° C., at 6.6 Pa) to yield (R)-2-methyl-4,4,4-trifluorobutylamine hydrochloride as a white solid (9.89 g, 88%); m.p. 187°–191° C.; partial NMR (300 MHz, DMSO-d$_6$-D$_2$O shake): 1.05 (d, 3H, CH$_3$), 2.06–2.36 (m, 2H, CF$_3$CH$_2$) 2.36–2.54 (m, 1H, CHCH$_3$) 2.73 (dd, 1H, CH$_2$N), 2.87 (dd, 1H, CH$_2$N) 8.20 (br, s, 2H, NH$_2$).

EXAMPLE 6

A solution of the product of Example 1b) (26.0 g, 100 mmol) and methyl 4-bromomethyl-3-methoxybenzoate (26.7 g, 103 mmol) in acetonitrile (66 ml) was heated to reflux for 3.3 h, the solvents removed at reduced pressure and the resulting dark brown gum stored under nitrogen for 18 h. The residue was dissolved in acetic acid (284 ml) and iron powder (16.6 g, 300 mmol) added. The mixture was heated at 100° C. for 2.5 h, cooled to room temperature, held at that temperature for 0.5 h, filtered and the residue washed with acetic acid (2×20 ml). Water (240 ml) was added to the combined filtrates over 20 min. and the mixture allowed to stand at room temperature for 66 h. The solidified residue was pulverised and filtered. The residue was recrystallized from methanol to afford 18.6 g of methyl 4-(5-methoxycarbonylindol-3-ylmethyl)-3-methoxy benzoate as a white solid.

FORMULAE

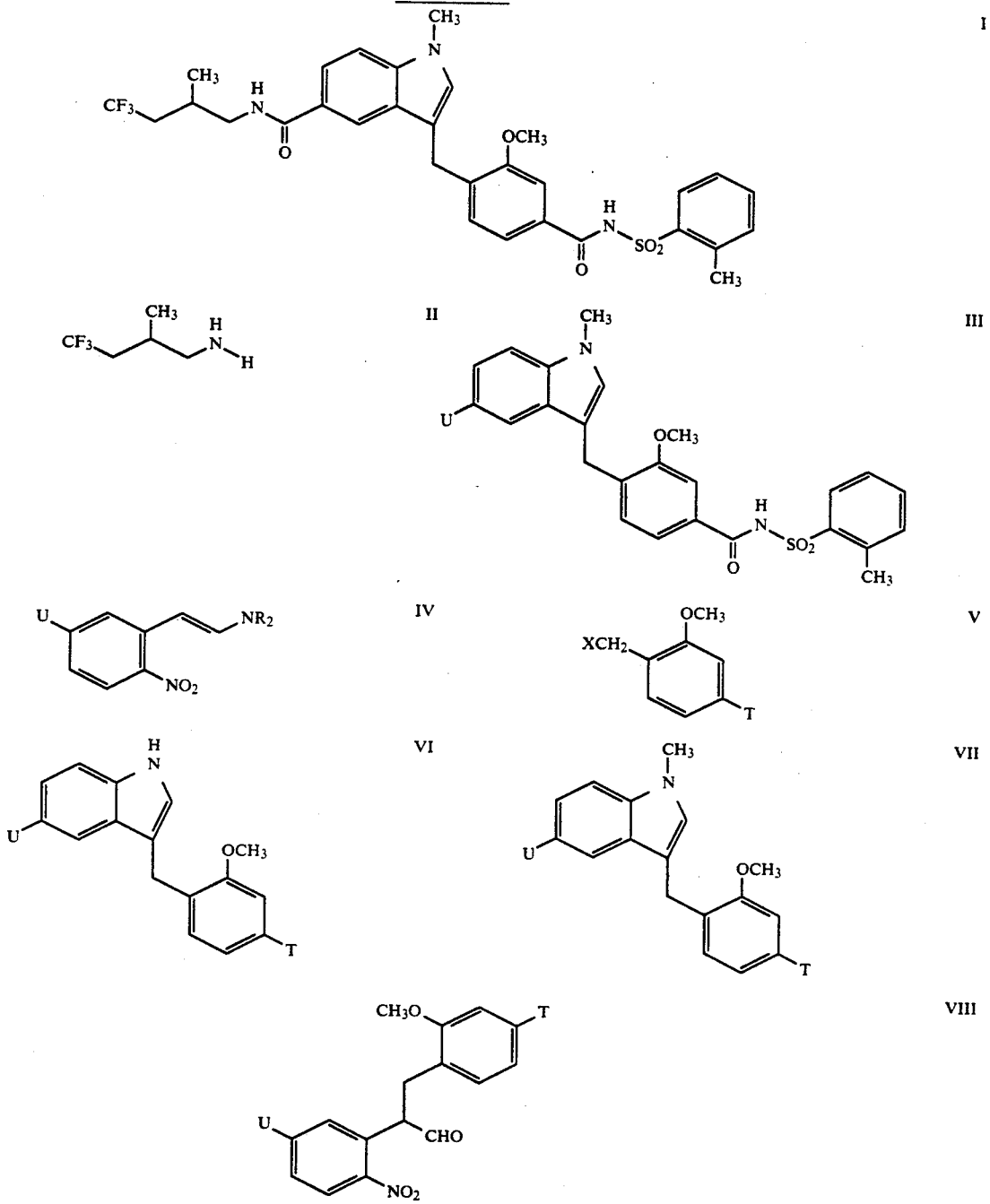

What we claimed is:

1. A process for the preparation of a 3-alkylated indole, which comprises:
   a) reacting a N-(2-nitrostyryl) enamine with an alkylating agent to afford an imine salt,
   b) optionally reacting the imine salt with water to afford a (2-nitrophenyl)acetaldehyde, and
   c) reacting the imine salt or the (2-nitrophenyl)acetaldehyde with a reducing agent capable of selectively reducing the nitro group, to afford the desired 3-alkylated indole.

2. A process as claimed in claim 1, in which the N-(2-nitrostyryl) enamine is a 2-nitro-β-(di(1–4C)alkylamino)styrene, a 2-nitro-β-(1-pyrrolidinyl)styrene, a 2-nitro-β-(1-piperidinyl)styrene or a 2-nitro-β-(4-morpholinyl)styrene.

3. A process as claimed in claim 1, in which the N-(2-nitrostyryl) enamine is a compound of formula IV

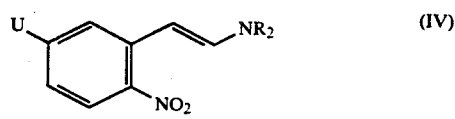

and the alkylating agent is a compound of formula V

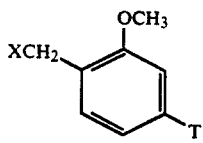

(V)

wherein each R independently represents a (1-4C)alkyl group or together represent a 4- or 5-membered alkylene or heteroalkylene chain, X is a leaving atom or group, T is COOR$^h$, U is COOR$^j$, and R$^h$ and R$^j$ are each independently a conveniently removed acid protecting group.

4. A process as claimed in claim 1 or 3, in which the imine salt is reacted with water to afford a (2-nitrophenyl)acetaldehyde.

5. A process as claimed in claim 1 or 3, in which the reducing agent is iron in the presence of an acid; stannous chloride; titanium trichloride; sodium dithionite; hydrazine with Raney nickel; or hydrogen in the presence of a transition metal hydrogenation catalyst.

6. A process as claimed in claim 4, in which the reducing agent is iron in the presence of an acid; stannous chloride; titanium trichloride; sodium dithionite; hydrazine with Raney nickel; or hydrogen in the presence of a transition metal hydrogenation catalyst.

7. A process as claimed in claim 5, in which the reducing agent is iron in the presence of acetic acid.

8. A process as claimed in claim 6, in which the reducing agent is iron in the presence of acetic acid.

9. A process as claimed in claim 1 or 3, in which the alkylation is effected at a temperature in the range of from 0° to 120° C., and the reduction is effected at a temperature in the range of from 0° to 120° C.

10. A process as claimed in claim 4, in which the alkylation is effected at a temperature in the range of from 0° to 120° C., and the reduction is effected at a temperature in the range of from 0° to 120° C.

11. A process as claimed in claim 1 or 3, in which the imine salt is reacted with water at a temperature in the range of from 0° to 100° C.

12. A process as claimed in claim 4, in which the imine salt is reacted with water at a temperature in the range of from 0° to 100° C.

* * * * *